United States Patent [19]

Blytas

[11] Patent Number: 4,599,178
[45] Date of Patent: Jul. 8, 1986

[54] RECOVERY OF GLYCERINE FROM SALINE WATERS

[75] Inventor: George C. Blytas, Houston, Tex.

[73] Assignee: Shell Oil Company, Houston, Tex.

[21] Appl. No.: 631,125

[22] Filed: Jul. 16, 1984

[51] Int. Cl.$^4$ ............................................. B01D 17/00
[52] U.S. Cl. ................................... 210/737; 210/259; 210/774
[58] Field of Search ...................... 210/651, 259, 500.2, 210/737, 774; 204/186, 301, 308

[56] References Cited

U.S. PATENT DOCUMENTS 3,228,877  1/1966  Mahon ........................ 210/500.2 X
3,704,223 11/1972  Dietzch et al. ...................... 204/301
3,715,402  2/1973  Louvar et al. .................. 204/186 X
4,036,749  7/1977  Anderson ........................ 204/186 X

FOREIGN PATENT DOCUMENTS 43-6079  6/1968  Japan ................................... 204/186

Primary Examiner—Frank Spear
Attorney, Agent, or Firm—Ronald R. Reper

[57] ABSTRACT

A process for recovery of glycerine from saline waters-containing glycerine comprises evaporating the water to precipitate a major amount of any salts present, separating the liquid phase and diluting it with water to low viscosity, electrodialysing the diluted liquid phase to obtain, (1) a concentrate stream which is recycled to the evaporative step, and (2) a diluate stream which is subjected to fractionation distillation to obtain glycerine as an overhead fraction.

5 Claims, No Drawings

RECOVERY OF GLYCERINE FROM SALINE WATERS

FIELD OF THE INVENTION

This invention relates to a process for the recovery of glycerine from saline water containing glycerine. It is particularly suited for treatment of saline waste water resulting from the manufacture of epoxy resins.

BACKGROUND OF THE INVENTION

Aqueous waste streams containing contaminating amounts of glycerine and polyglycerides are generated in a variety of industrial processes, for example, in the manufacture of epoxy resins. Before such aqueous streams can be discharged into a receiving stream, the organic content must be substantially reduced in order to meet regulatory standards. For example, the production of epoxy resins by reaction of epichlorohydrin and bisphenol may result in an aqueous waste stream containing not only small amounts of glycerine and polyglycerides but in addition inorganic salts of alkali and/or alkaline earth metals. Disposal of such waste streams is both difficult and expensive owing to the presence of the metal salts which engender corrosion/fouling problems for disposal by incineration and of the polyglycerides (telomers of glycerine) which are refractory to biodegradation. Further it is very desirable to recover much of the valuable glycerine.

SUMMARY OF THE INVENTION

The invention provides a process for recovering glycerine from a glycerine-containing saline aqueous stream which process comprises:
  (a) evaporating the feed stream to remove water and to precipitate at least about 85% of the salt content of the feed stream,
  (b) separating the liquid phase from the precipitated salt,
  (c) diluting the liquid phase product of step b in a dilution zone with a salt-free aqueous stream to obtain a diluted liquid phase product having a viscosity less than about 10 centipoise,
  (d) subjecting the product of step c to an electrodialysis step in which the saline components migrate through fixed anion and cation exchange membranes to a concentrate stream or streams, leaving a diluate stream or streams reduced in saline content,
  (e) recycling at least part of the concentrate stream from step (d) to the evaporation step (a), and
  (f) recovering glycerine from the diluate stream of step d by fractional distillation.

DESCRIPTION OF PREFERRED EMBODIMENTS

In accordance with the invention, a saline aqueous stream containing small amounts e.g., from about 1 to about 7% w glycerine is treated to economically recover the glycerine and to substantially reduce problems relating to the disposal of the stream. Disposal of such streams containing significant amounts of metal salts of alkali and/or alkaline earth metals such as sodium chloride and calcium chloride in both difficult and expensive owing to the presence of minor, but significant amounts of water soluble organic materials such as glycerine. Further, the recovery and sale of valuable glycerine having utility in a wide variety of applications such as alkyds, tobacco, cellophane, drugs and toilet goods, reduces the overall expense related to the disposal problem.

The process is particularly suitable for treating saline waste streams arising from the manufacture of epoxy resins e.g., by reaction of epichlorohydrin and bisphenol A. Such streams typically contain minor amounts e.g., about 1 to about 7% w glycerine together with some glycerine telomers, and significant amounts e.g., up to about 16% w salts of alkali and/or alkaline earth metals. Exemplary salts are the carbonates, chlorides and bromides of metals, such as, sodium, potassium, lithium, calcium and barium. In general, the process uses highly efficient evaporation equipment and procedures to remove water to precipitate a major amount, at least about 85% of the inorganic salt content. Such evaporation techniques are not part of the invention, but are well known to those skilled in the art. Exemplary techniques include single or multiple effect short tube evaporators (calandrias) which typically operate under vacuum. The most economical selection between single and multiple effect evaporation usually will depend upon the cost of steam and the total evaporative load. Where energy costs are very expensive, the use of steam vapor recompression techniques may be suitably employed.

It is preferred to use vapor compression evaporation methods. Since each stage of such a process is limited as to the extent of water removal, it becomes appropriate to use several stages of vapor compression evaporation in series, or at least one vapor compression unit followed by one or more evaporator effects.

The precipitated salt(s) may be separated from the liquid phase by known techniques e.g., filtration, centrifugation, decantation and the like, and disposed of as such, or subjected to further treatment, as desired Ordinarily the separated liquid phase will have become highly viscous owing to the concentration of glycerine, and possibly other organic materials such as glycerine telomers and the like. Accordingly, the separated liquid phase will be diluted, with water to a viscosity less than about 10 centipoise at 30° C., and preferably less than about 8 centipoise. Excellent results in subsequent processing have been achieved when the separated liquid phase has been diluted with water and/or condensate to a viscosity less than about 6 centipoise at 30° C. It will be noted that according to the invention, a majority of the inorganic salts are first removed prior to the electrodialysis step thereby permitting high efficiency in terms of electrical power utilization while minimizing requirements for expensive membrane surface area that would otherwise be required. As will be apparent to those skilled in the art, condensate from the evaporation step a may be suitably employed in step c to dilute the liquid phase product of step b. Generally speaking, the amount of water and/or condensate added to the liquid phase from step b will be in the weight ratio from about 0.5:1 to about 1.5:1 water to liquid phase, with ratios in the range from about 0.8:1 to about 1.3:1 being preferred.

Electrodialysis is by now a well established industrial process. Basically, an electrodialysis unit comprises a plurality of membranes alternately anionic and cationic placed between an anode and a cathode connected to a direct current source. The membranes are usually separated from each other by 2 to 5 mm using appropriate spacers and the feed stream may be made to flow through a spacer creating a turbulent path in order to increase turbulence of the liquids contacting the membranes or insheet-type flow to reduce pumping pressure. The construction of the unit is generally in the form of a stack, like a filter stack. The membranes which usually contain ion exchange groups have a fixed positive or negative charge. The cationic membranes have negative fixed charges; the anionic membranes have positive fixed charges. Electrical neutrality in the membrane matrix is satisfied by the migrating cations (through cationic membranes) and anions, (through anionic exchange membranes).

When a direct current is applied across the two electrodes (anode and cathode) anions will tend to migrate towards the anode passing through the anion exchange membrane and being stopped by the first cation exchange membrane. In like manner, cations will cross through the cationic exchange membrane and will be stopped by the anionic exchange membranes. However, non-electrolyte species are not prevented from passing through the exchange membranes, except in so far as these are made of a tighter pore structure, even so, however, non-electrolytes will migrate through the membranes, the actual amount of migration depending on relative volumes of diluate/concentrate.

If a feed stream is introduced uniformly from the top of the electrodialysis unit, it will be found that passages in the unit having an anion membrane on the cathode side of the passage and vice versa will become concentrate streams richer in ionized (herein saline) components and the other streams in passages bounded by anion membranes on the anode side and cathode membranes on the cathode side will become depleted in ionized components. Such depleted stream or streams are herein referred to as the diluate stream.

The cation- and anion-exchange membranes can be any cation- and anion-selective membranes respectively, which are capable of withstanding the components in the feed water. Examples of suitable membranes are disclosed in the article entitled "Electrodialysis", Kirkothmer Encyclopedia of Science and Technology, pages 846–865 (2nd edition, Interscience Publishers 1965). Suitable membranes may be obtained from Ionics Incorporated, 152 Sixth St, Cambridge, Mass. The cation membranes may for instance comprise an insoluble ion-exchange material of cross-linked sulfonated co-polymers of vinyl compounds either in the form of a homogeneous sheet or cast on a matrix of synthetic reinforcing fabrics. Such a membrane is sold by the above company under the reference "TYPE 61 CZL 386". The anion membrane may comprise an insoluble ion-exchange material of cross-linked copolymers of vinyl monomers containing quaternary ammonium anion exchange groups either in the form of a homogeneous sheet or cast on a matrix of synthetic reinforcing fabrics. Such a membrane is obtainable from the above company under the reference "TYPE 103 AZL 386".

Generally, for stability of the membranes, it is necessary to employ temperatures below about 70° C. during electrodialysis. While in terms of electrical efficiency it would be preferred to carry out the electrodialysis step at about 50° C., experience thus far has shown best results are obtained at a temperature in the range from about 20 to 40° C., especially 25 to 35° C.

As stated above, electrodialysis membranes, which are selective for anionic or cationic species, are nevertheless non-selective towards rejection of non-electrolytes. In the present case, glycerine, a nonelectrolyte, can diffuse through the anion and cation exchange and leave the electrodialysis unit with the concentrate stream (into which the salts are concentrated) so as to leave a salt-free dilute stream. In this fashion amounts e.g., up to about 20% w of the glycerine will migrate through the electrodialysis membranes and be lost in the concentrate stream. According to the invention, all or part of the concentrate stream is recycled to the evaporative step a of the process to recover this glycerine. Of course, to prevent undue accumulation of materials in the process system, a periodic or continuous small purge of the concentrate stream will be needed when the concentrate is substantially entirely recycled to the evaporation step a. Generally, the concentrate stream will be returned at an appropriate early evaporative stage of step a.

In order to recover glycerine therefrom, the diluate stream obtained after electrodialysis, is subjected to fractional distillation to separate water as a top fraction, glycerine as an intermediate fraction, and high boiling components as a residual fraction. In a preferred embodiment, the fractional distillation zone may comprise first a single effect evaporator for efficient water removal, and second, a fractional distillation column. The substantially water-free product of the evaporation is fractionated in the column to remove glycerine as the overhead fraction and high boiling polyglycerides and the like are obtained as the residual fraction. It is an advantage of the instant process that the salt-free heavy ends may be conveniently burned to recover the heat value thereof without the corrosive effects of high salt concentration, or maybe subjected to further purification, for use in coatings and the like. Also, the use of electrodialytic desalting prior to glycerine overheading avoids the presence of solid, precipitated salts in the bottoms fraction of the glycerine distillation column.

The invention is further illustrated but is not intended to be limited by the following hypothetical example:

An aqueous waste stream from a process for the manufacture of epoxy resins by reaction of epichlorohydrin with bisphenol A is used as feed to the process according to the invention. The aqueous stream having a pH of about 10 contains 1.8% w glycerine, 8% w sodium chloride, about 0.6% w telomers (mostly dimers and trimers of glycerine), less than about 0.4% w of other organic materials having boiling point below that of water and 88.2% w water.

Water and the low boiling materials are evaporatively removed with high energy efficiency by a combination of vapor recompression/multiple effect evaporation to remove at least about 95% of the water originally present, resulting in crystallization/precipitation of about 95% of the salt originally present. The liquid phase, which is separated from the crystalline solid by centrifugation, is found to contain about 60% w glycerine, 6.8% w salt, 6% w water and 27.2% w telomers of glycerine. The liquid phase which has a viscosity of about 100 centipoise is diluted with water in a diluting zone, which may be a stirred vessel, in a volume ratio of about 1:1 water to liquid phase to reduce the viscosity to about 6 centipoise at 30° C. The diluted liquid phase is then fed to an electrodialysis unit comprised of alternating anionic exchange membranes 103 PZL 386 and cation exchange membranes 61 AZL 386 which membranes are available from Ionics Incorporated. About 89% w of the salt (as NaCl) in the feed is removed at an electric power consumption of about 0.5 Kw-m/lb of NaCl removed. In general, the voltage across each stack of membranes is arranged so that there is a voltage of about 1.5 volts per cell pair. The concentrate stream from the electrodialysis unit contains about 75.3% w water, 8% w salt, 12% w glycerine and 4.3% w telomers of glycerine. The concentrate stream is recycled back to the evaporation step a in order to precipitate the salt and to permit higher recovery of the original glycerine which might otherwise be lost upon disposal of the concentrate stream. The diluate stream containing about 30% w glycerine, less than 0.3% w of sodium chloride, about 9% w telomers of glycerine and balance water is passed to a two-stage fractional distillation zone. The first stage comprises a single effect evaporator which the evaporator product to a fractional distillation column which removes as overhead glycerine having a purity in the range from about 83–93% w (along with some diglycerol impurities) and yields a bottom fraction containing about 93.5% w telomers of glycerine, 6% w glycerine and about 3% w sodium chloride.

More thorough desalting can be done by continuing electrodialysis over a longer period of time. This increases the power consumption per lb of NaCl removed, and results in more concentrated salts in the concentrate.

I claim:

1. A process for recovering glycerine from a saline aqueous stream resulting from the manufacture of epoxy resins and containing from about 1 to about 7% w glycerine and at least about 5% w sodium chloride which process comprises:

(a) evaporating the feed stream to remove water and to precipitate at least about 85% of the salt content of the feed stream,
   (b) separating the liquid phase from the precipitated salt,
   (c) diluting the liquid phase product of step b in a detention zone with an aqueous stream to obtain a diluted liquid phase product having a viscosity less than about 10 centipoise,
   (d) subjecting the product of step c to an electrodialysis step in which the saline components migrate through fixed anion and cation exchange membranes to a concentrate stream or streams leaving a diluate stream or streams reduced in saline content,
   (e) recycling the concentrate stream from step d to the evaporating step a, and
   (f) recovering glycerine from the diluate stream of step d by fractional distillation.

2. A process is in claim 1, wherein step (a) an amount of water is evaporated so as to precipate at least about 90% of total inorganic salt content of the feed stream.

3. A process as in claim 1, wherein step (c) the liquid phase product is diluted with water to a obtain liquid phase product having a viscosity less than about 8 centipoise.

4. A process as in claim 1, wherein step (e) comprises: (1) removing substantially all water from the diluate stream, then fractionally distilling the substantially water-free product and recovering glycerine as an overhead product.

5. A process as in claim 1 wherein the saline aqueous stream contains up to about 16% w salts of alkali and/or alkaline earth metals.

* * * * *